D. Bly,
Artificial Leg,
No. 1,724, Reissued July 12, 1864.
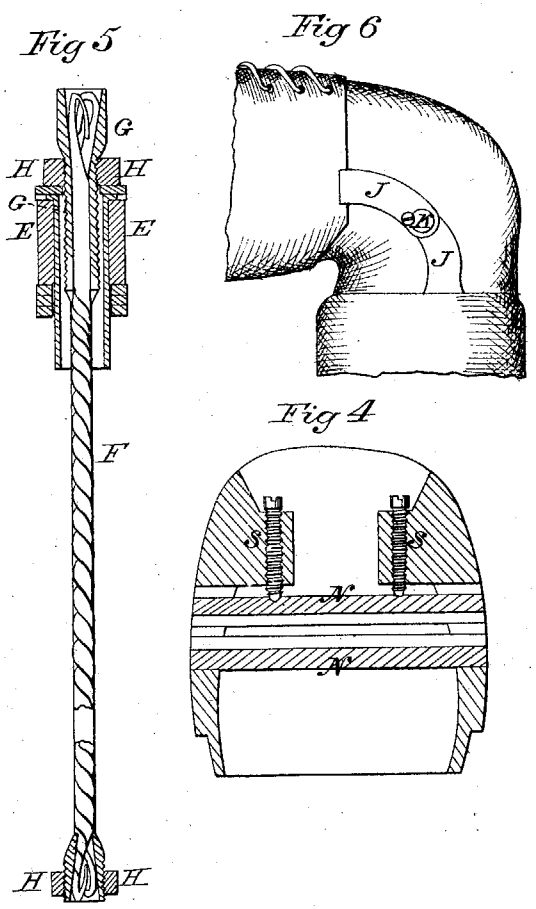
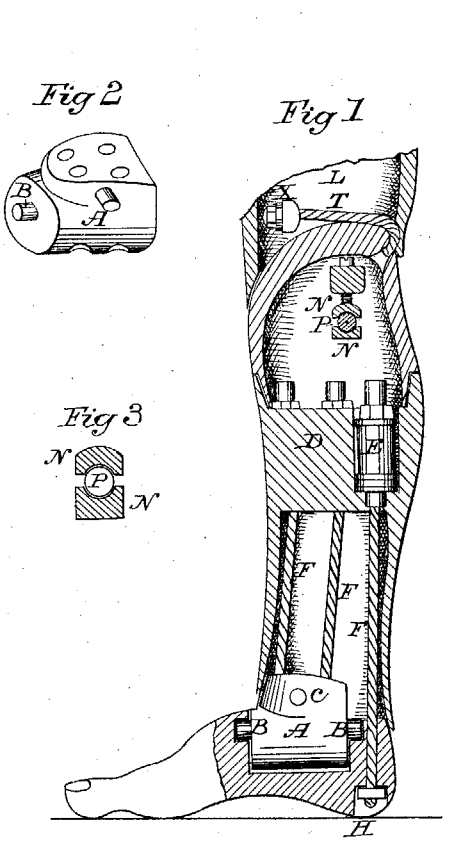
Witnesses:
J. Fraser.
J. M. Holloway.
Inventor.
Douglas Bly M.D.
AM. PHOTO-LITHO. CO. N.Y. (OSBORNE'S PROCESS.)

UNITED STATES PATENT OFFICE.

DOUGLAS BLY, OF ROCHESTER, NEW YORK.

IMPROVEMENT IN ARTIFICIAL LEGS.

Specification forming part of Letters Patent No. 24,002, dated May 17, 1859; Reissue No. 994, dated July 3, 1860; Reissue No. 1,367, dated December 23, 1862; Reissue No. 1,721, dated July 12, 1864.

*To all whom it may concern:*

Be it known that I, DOUGLAS BLY, of the city of Rochester, in the county of Monroe and State of New York, have invented certain new and useful Improvements in the Construction of Artificial Legs, of which the following is a full and accurate description, reference being had to the accompanying drawings, making a part of these specifications, and the letters of reference marked thereon.

Same letters referring to like parts in all the figures of said drawings.

Figure 1 is a vertical section showing the mode of constructing the leg. Fig. 2 is the portion which forms the ankle-joint, detached from the other parts. Fig. 3 is a transverse section of the box and bolt at knee-joint. Fig. 4 is a longitudinal section of the box, showing its relative position. Fig. 5 is a view showing the manner of fastening the ends and regulating the tension of the cords. Fig. 6 is a view of the curved metallic straps or bars used when amputation has taken place below the knee.

Before proceeding to describe my artificial leg as now constructed, I would state that I have only arrived at it after a series of laborious and expensive experiments.

The nature of this invention consists in a certain arrangement and combination of parts whereby a more perfect substitute is obtained for the natural leg. The action of the latter, as provided for by various muscles, tendons, and joints, being simulated by simple substances, is represented in the accompanying drawings.

In ordinary walking the power of moving the ankle-joint in all directions is necessary to ease and grace. Different parts of the foot may be placed on little elevations or depressions in the ground or on sticks and stones, which makes it necessary that the ankle-joint should move more or less in all directions, so that the foot can accommodate itself to the inequalities of the surface. When walking, the toes are turned outward, so that the line of flexion of the ankle-joint is not in a right line with the foot, but in a line with the ball of the great toe, which requires a diagonal flexion. By providing for this, the fatiguing and uncouth halt, which is so often seen in those wearing artificial legs, is avoided. It is necessary that the ankle-joint should flex sidewise or laterally when an effort is made to lift a heavy weight, as the feet are then spread far apart and the legs are no longer perpendicular to the soles of the feet. Indeed this is the case in almost all kinds of labor, as the feet are then generally spread far apart, to give a wide base of support, as seen in planing, filing, sawing, &c. In the natural limb means are provided not only for flexing the foot, on the leg antero-posteriorly, but diagonally, as in ordinary walking, with the toes turned outward, and sidewise or laterally, as in many positions assumed in labor, or when one side of the foot is placed on elevations or depressions in the ground.

I provide for all these motions by constructing the ankle-joint as follows: The ankle-joint is formed by a body, A, which represents the astragalus (the upper-bone of the foot.) This body has an antero-posterior axis and a lateral axis connecting it, respectively, with the foot and leg. The antero-posterior axis takes bearings in the foot. This allows a free and easy lateral motion. The lateral axis takes bearings in the leg D, and allows a free and easy antero-posterior motion. These two motions and their combinations produce motion in all directions required in the use of ankle-joint in an artificial leg. The joint thus constructed allows the foot to be flexed on the leg at every point of the circle, and at the same time, from the fixed nature of the axes, prevents the foot from rotating horizontally. These axial movements are effected by means of bolts or pivots B C, or their equivalents, situated in the body A and having their projecting ends serve as journals or bearings, which rest, respectively, in the foot and leg. The bolts or pivots may either be fixed in the body A and turn in the foot and leg, or be fixed in the foot and leg and turn in the body A. The body A may have any desired or convenient shape (whether strictly as a body or not) which will enable its functions to be fulfilled—namely, to furnish a common support to and form a connection between the journals of the bolts or pivots B C.

When the axial bolts are made to turn or move in the body A, it is required to be of considerable size to give sufficient bearing-surface. Much, however, depends upon the material used, which may be steel, iron, brass, composition of metals, vulcanized india-rubber, wood, or any material desired. That is best which combines sufficient strength and durability with the least weight.

When the axial bolts are made to turn in the leg and foot, the body A may be only a mass without reference to form, which connects the transverse axes and harmonizes their movements. It may be perforated in the center to give it lightness, or for the passage of a cord or cords, or in any other part consistent with strength, or it may be reduced in size until it is merely the common union of the antero-posterior and lateral axial bolts at their intersection. These transverse axes may be on the same or different planes, and of equal or unequal lengths.

I have also introduced elements which are as nearly as possible equivalent in their actions to those of the tibialis, anticus, and posticus muscles, the Peroneus, tertius, longus, and brevis muscles, and the gastrocnemius and soleus muscles and their tendons. The muscles are simiuated by springs E made of caoutchouc, or other equivalent material, the elastic action of which is produced by compressing its mass. The advantages of such springs used in this manner are decided and important, first, since they are used by compression they cannot be overtaxed or broken; second, their actions are more uniform, soft, and easy, like the natural muscles; third, they never rust; fourth, they never rattle; and fifth, they require no oil, and the tendons are simulated by non-elastic cords F, attached to the springs, these being kept sufficiently tense to retain the foot in its normal position in relation to the leg, while at the same time, by means of the joint above described, the foot may be moved in any required direction. The ends of the cords are secured and their tension regulated by means of the screw G and nut H. The screw is tubular, the upper end of its surface being enlarged conically, and the fibers or strands at the ends of the cord, being dipped in glue or other suitable cement, are folded back upon it, forming an enlargement, which is trimmed to a concical form when it has been indurated by drying and drawn into the tube until so compressed as to yield no further. Before inserting, glue may be again applied to secure adhesion to the tube, which, being thus firmly secured to the cord and having a screw-thread cut on its exterior surface corresponding with that of the nut H, which rests on the top of the spring E, is thereby supported in it. Before putting the screw G through the spring E a thimble, Q, or tube with a flange on its upper end, is slipped over the screw, as shown in Fig. 5, to prevent the screw from coming in contact with or wearing the spring. By turning the nut the screw G is raised or lowered, by which the tension of the end is regulated with the greatest nicety. These springs are placed in recesses or cavities R, Fig. 1, which bear important relations to the springs themselves, and really govern their actions and limit the movements of the leg.

When the springs are compressed, the lateral expansion at first takes place mostly in the central position of the springs, and afterward nearer the ends, and so on, until the cavity is filled, if sufficient power or pressure is applied. Therefore the motion of the leg begins to be retarded when the expansion of the central portion of the spring begins to be limited by the cavity, and so on until the spring throughout its length is brought into contact with the side of the cavity. Consequently the motions of the leg are stopped by degrees, slowly and softly, without sudden jar or pain to the wearer. The springs and cavities may be of any suitable form, but each spring and its cavity should have nearly the same form.

By adjusting the relations of the size of the springs and the size of the cavities in which they are placed, the motions of the leg may be regulated and controlled with great accuracy.

Another object is gained by placing the springs in cavities—namely, a perfect support to the springs, which protects them against injury from overaction.

The object in placing the cords and springs in positions corresponding with those of the natural muscles is to perfect the mechanical arrangements and to steady the motions, since in order to secure steadiness it is absolutely necessary that the foot be retained in its normal position by two opposite yielding forces. In the natural limb this is attained by the antagonistic muscles.

When amputation has taken place below the knee-joint, the knee of the artificial leg is formed by two jointed metallic straps on bars J, one on each side. Each of these straps consists of an upper and lower section, which are connected by means of a mortise-and-tenon joint, and move upon the pivots on axes K. The lower end of the upper section and the upper end of the lower section are curved backward, so as to carry the joint or hinge back of a right line, and thereby simulate the shape of the bones of the natural leg and obtain a joint which works in harmony with the natural one, which is an important improvement. Furthermore, by means of this curve, the metallic straps conform to the contour of the natural limb when it is flexed and prevents the joints from pressing the parts forward in an unseemly manner when sitting, and from chafing and cutting them. Furthermore, by means of this curve, I am able to increase the distance between the pivot K and the anterior portions of the mortise and tenon, which come in contact, and form a stop to the joint, the benefit of which is twofold—increased stability when standing, and less liability of the parts which come in contact to wear.

When amputation has been performed above the knee, the knee-joint is formed by means of bolt and axis P, supported at each end, together with bearings in the blocks N N, which may be of any suitable material.

The bearing-surfaces in the blocks N N are longitudinal grooves, being segments of a cylinder, which coincides with and fits on the axial bolt. These two segment-bearings together do not cover the whole circumference of the axial bolt, therefore friction takes place on a correspondingly small surface, and consequently is reduced to a minimum. When the axial bolt is pressed into a simple bearing-aperture surrounding the whole circumference of the bolt with sufficient force to prevent looseness, and more friction is produced on all sides, and consequently is greater than in the device just described, one of the blocks, N N, should be fixed, the other movable. Two screws, S S, are arranged so as to tighten the bearing-surfaces of the blocks against the axial bolt, in order to regulate the friction, and prevent looseness and noise, and jar from lost motion.

When the leg moves from a flexed to a straight position, the motion of the knee-joint is limited and controlled by means of the cord T and spring X, formed like those before described in this specification. One end of this cord is attached to the posterior superior portion of the leg D, and the other end to a cross-bar in the anterior inferior portion of the thigh L. By placing the cord in this position it is brought nearly in line with the strain or draft, which enables it to control or limit the motions of the joint with facility, and the spring prevents any jar, which otherwise might arise from stopping the motion too suddenly. It also prevents the appearance of sudden mechanical action and renders it more like that of nature.

What I claim as new, and desire to secure by Letters Patent, is—

1. Curving or deflecting the jointed extremities of the bars J so as to bring their axis of motion back of their line of direction, substantially as and for the purposes set forth.

2. The cord T and spring X, acting upon the parts D and L, substantially in the manner and for the purpose herein set forth.

3. I am aware that metallic springs have been employed to simulate the functions of the natural muscles, but experience has proved their inadequacy, both as respects the results obtained and their durability. I am also aware that india-rubber or elastic cords have been used for the same purpose and with no better results, and these I do not claim; but I claim the combination of the india-rubber spring E, with a tendon or cord, in such a manner that the required effect is derived from the compression and expansion of the material and not from its elongations and contractions, substantially as set forth.

4. Placing the spring of caoutchouc, or equivalent material, which acts from the compression of its mass, in a chamber or cavity which has such a size or diameter, in relation to that of the springs, as to regulate and check the compression of the spring at the required limit of the motion of the limb, and protects the spring from overaction.

5. The axial bolts or transverse axes B C, as and for the purpose herein set forth.

6. Providing the ends of cords F with the enlargements, and with the conical socket-fastenings G to receive the same, substantially as described, in order to apply adjusting-screws for the purposes herein specified.

7. The manner of constructing the bearing portions of the knee-joint, consisting of the upper and lower bearing-blocks, N N, each of which forms a segment of a cylinder more or less corresponding with the axial bolt, the one being fixed in position and the other adjustable by means of the screws S S, to admit of adjusting the parts together to prevent looseness and noise and to reduce and regulate the friction, substantially as and for the purpose herein set forth.

DOUGLAS BLY.

Witnesses:
J. S. BROWN,
JNO. D. PATTEN.